(12) United States Patent
Kaeppler et al.

(10) Patent No.: US 7,816,569 B2
(45) Date of Patent: Oct. 19, 2010

(54) PROCESS FOR THE PREPARATION OF CHLOROMETHANE USING RECYCLED HYDROGEN CHLORIDE

(75) Inventors: Klaus Kaeppler, Burghausen (DE); Gerhard Nagy, Handenberg (AU)

(73) Assignee: Wacker Chemie AG, Munich (DE)

( * ) Notice: Subject to any disclaimer, the term of this patent is extended or adjusted under 35 U.S.C. 154(b) by 361 days.

(21) Appl. No.: 12/119,564

(22) Filed: May 13, 2008

(65) Prior Publication Data

US 2008/0287716 A1 Nov. 20, 2008

(30) Foreign Application Priority Data

May 16, 2007 (DE) ........................ 10 2007 023 052

(51) Int. Cl.
*C07C 17/00* (2006.01)
(52) U.S. Cl. ..................................... 570/181
(58) Field of Classification Search ................... 570/181
See application file for complete search history.

(56) References Cited

U.S. PATENT DOCUMENTS

| 4,032,557 A | 6/1977 | Spork et al. |
| 5,202,512 A | 4/1993 | Winkler et al. |

FOREIGN PATENT DOCUMENTS

| DE | 2 521 742 A | 11/1976 |
| DE | 2521742 | 11/1976 |
| DE | 3146526 A | 8/1982 |
| EP | 0 428 166 A | 5/1991 |
| EP | 0428166 A | 5/1991 |

OTHER PUBLICATIONS

Lehnert, R., Nachr. Chem. Tech. Lab 2009(09), 1167-1168.

*Primary Examiner*—Deborah D Carr
(74) *Attorney, Agent, or Firm*—Brooks Kushman P.C.

(57) ABSTRACT

The invention relates to a process for the preparation of chloromethane from methanol and hydrogen chloride contaminated with Si compounds, the Si compounds being methylchlorosilanes, methoxymethylsilanes and hydrolysis and condensation products thereof, in which some of the Si compounds are removed by condensation from the chloromethane formed and remaining Si compounds are washed out with methanol, the methanol thus obtained and containing Si compounds being used for the further preparation of chloromethane with hydrogen chloride.

9 Claims, 2 Drawing Sheets

PROCESS FOR THE PREPARATION OF CHLOROMETHANE USING RECYCLED HYDROGEN CHLORIDE

BACKGROUND OF THE INVENTION

1. Field of the Invention

The invention relates to a process for the preparation of chloromethane from methanol and hydrogen chloride contaminated with silicon compounds.

2. Background Art

For the preparation of chloromethane from methanol and hydrogen chloride which originates from the methylchlorosilane hydrolysis, silicon compounds are introduced into the chloromethane reactor. The distillate of the chloromethane reactors therefore contains, as an undesired impurity, methylchlorosilanes, methoxymethylsilanes, hydrolysis and condensation products (polymethylsiloxanes) thereof (referred to collectively as Si compounds below) and hydrocarbons formed as a by product in the methylchlorosilane synthesis (Müller-Rochow). Cyclic polydimethylsiloxanes such as hexamethylcyclotrisiloxane (D3), octamethylcyclotetrasiloxane (D4) and decamethylcyclopentasiloxane (D5), in particular D4, are the main constituent of the Si compounds. These Si compounds cannot be adequately separated from the chloromethane gas by condensation. A portion of the Si compounds condenses in the water scrubber and is fed together with the outflowing MeOH/water mixture to the distillation for methanol recovery. The other portion of the Si compounds is stripped out from the water scrubber together with the MeCl and then converted into siloxanyl sulfates in the drying of the MeCl in the sulfuric acid scrubber. The content of siloxanyl sulfates complicates the disposal or the recycling of the sulfuric acid since silica-like solids which are difficult to handle are formed. The Si compounds fed to the distillative methanol recovery with the methanol/hydrochloric acid mixture leave the column partly together with dilute hydrochloric acid in the form of siloxanols. The other portion of the Si compounds is transported back into the MeCl reactor together with the methanol recovered as the overhead product.

Siloxane producers lose many tonnes per year of Si compounds via the wastewater and especially via the sulfuric acid. These Si compounds cause problems in the handling of the sulfuric acid used for drying and additionally contaminate the environment with poorly biodegradable organosilicon components.

The 1st stage of the hydrolysis of dimethyldichlorosilane to polydimethylsiloxanes is frequently carried out with a substantially stoichiometric amount of water, i.e. with 1 mol of water per 1 mol of $Me_2SiCl_2$. In this procedure, the chlorine present in the organochlorosilane is not obtained in the form of hydrochloric acid but in the form of substantially dry hydrogen chloride gas. The energy-consumptive production of hydrogen chloride from hydrochloric acid is then not necessary. Hydrogen chloride gas is required for the preparation of MeCl, which in turn is used for the preparation of methylchlorosilanes from Si.

All hydrolysis processes of organochlorosilanes which give hydrogen chloride gas directly have, however, the disadvantage that the hydrogen chloride obtained is contaminated with silicon compounds and hydrocarbons. The purification of hydrogen chloride which is obtained in plants producing chlorosilanes or siloxanes and contains Si compounds and/or alcohols as an impurity is effected in general by washing the gas mixture with a wash liquid, such as water, hydrochloric acid or sulfuric acid. The purification of hydrogen chloride by distillation is also described. Little has been reported to date about the purification of hydrogen chloride from the hydrolysis process of dimethyldichlorosilane, which contains Si compounds and hydrocarbons.

In an integrated plant for the preparation of $\alpha,\omega$-dihydroxypolydimethylsiloxanes, cyclic polydimethylsiloxanes and MeCl, it is possible to use $\alpha,\omega$-polydimethylsiloxanes as a purification liquid for separating off Si compounds from HCl gas. In this procedure, however, numerous unsolved secondary problems occur owing to the reactivity of the $\alpha,\omega$-dihydroxypolydimethylsiloxanes.

Owing to the insufficient purity of the hydrogen chloride originating from the organochlorosilane hydrolysis, the hydrogen chloride can be converted into MeCl only in liquid-phase processes with methanol. The distinction is made between catalyzed and uncatalyzed liquid-phase processes. The choice of the catalysts for the liquid-phase processes is limited owing to the impurities in the hydrogen chloride. However, catalyzed processes have the advantage of higher space-time yields and higher yields with respect to methanol and HCl. The catalysts frequently used in liquid-phase processes are metal chlorides having Lewis acid properties, such as zinc chloride, iron chloride, bismuth oxychloride, or amines, or quaternary ammonium or phosphonium compounds.

A liquid-phase process for the preparation of MeCl with the use of hydrogen chloride (gas) and methanol is described, for example, in EP 0 428 166 A1. However, the quality of the hydrogen chloride used is not discussed there. Si compounds introduced via the hydrogen chloride must enter the process either in the product MeCl or via the resulting water of reaction, as wastewater depending on the pressure/-temperature conditions prevailing in the MeCl reactor. Where the Si compounds entrained via the hydrochloric acid used or the hydrogen chloride gas remain or how they are treated is not described. In some cases, the processes described in the literature were tested only in laboratory experiments. Problems with Si compounds present in low concentration are not recognized here. The further processing of the MeCl or the distillative recovery of MeOH used in excess is not described.

In the distillative working-up of the mixtures of water, MeOH, HCl and Si compounds inevitably obtained in the MeCl synthesis, the Si compounds frequently polymerize. Blockage occurs in apparatuses and pipelines. The heat transport in heat exchangers may be hindered. The Si compounds remaining in the process wastewater are not biodegradable and cause so-called "persistent COD". Such Si compounds should be avoided in wastewater for environmental reasons.

MeCl contaminated by Si compounds cannot be used as a raw material for the direct synthesis of organochlorosilanes from MeCl and Si. The separation of Si compounds from MeCl requires additional complicated separation methods, e.g. distillations. If the Si compounds are not removed from the MeCl, they cause problems by formation of silica-like solids in the frequently used treatment with concentrated sulfuric acid for removing dimethyl ether (DME) and for drying.

The unreliability of the process increases as a result of the Si compounds entrained into the MeCl synthesis. A loss of siloxane is observed, which reduces the yield of the process. The environment is polluted.

In the so-called methanolysis processes of methylchlorosilanes, the Si-bonded chlorine is converted directly into MeCl by reaction with methanol/water mixtures. In these processes, too, an MeCl contaminated with Si compounds may be obtained. DE 2521742 A1 describes such a process. The mixture of MeCl, MeOH, HCl and DME leaving the reactor is partly condensed and the noncondensing constituents are washed with methanol cooled to 12° C. The methanol scrubber apparently serves for separating off water, HCl and DME from the MeCl. No information is given regarding the composition of the material streams fed to and removed from the scrubber.

DE 3146526 A1 describes a methanolysis process in which Si-containing MeCl is removed as a vapor mixture from the reactor. A part of the Si compounds present in the MeCl is removed by condensation. Nothing is said about the residual content of Si compounds and the further processing of the MeCl.

SUMMARY OF THE INVENTION

The invention relates to a process for the preparation of chloromethane from methanol and hydrogen chloride contaminated with Si compounds, the Si compounds being selected from methylchlorosilanes, methoxymethylsilanes and hydrolysis and condensation products thereof, in which some of the Si compounds are removed by condensation from the chloromethane formed and remaining Si compounds are washed out with methanol and the methanol thus obtained and containing Si compounds is used for the preparation of chloromethane with hydrogen chloride.

DETAILED DESCRIPTION OF THE PREFERRED EMBODIMENT(S)

Figure 1:
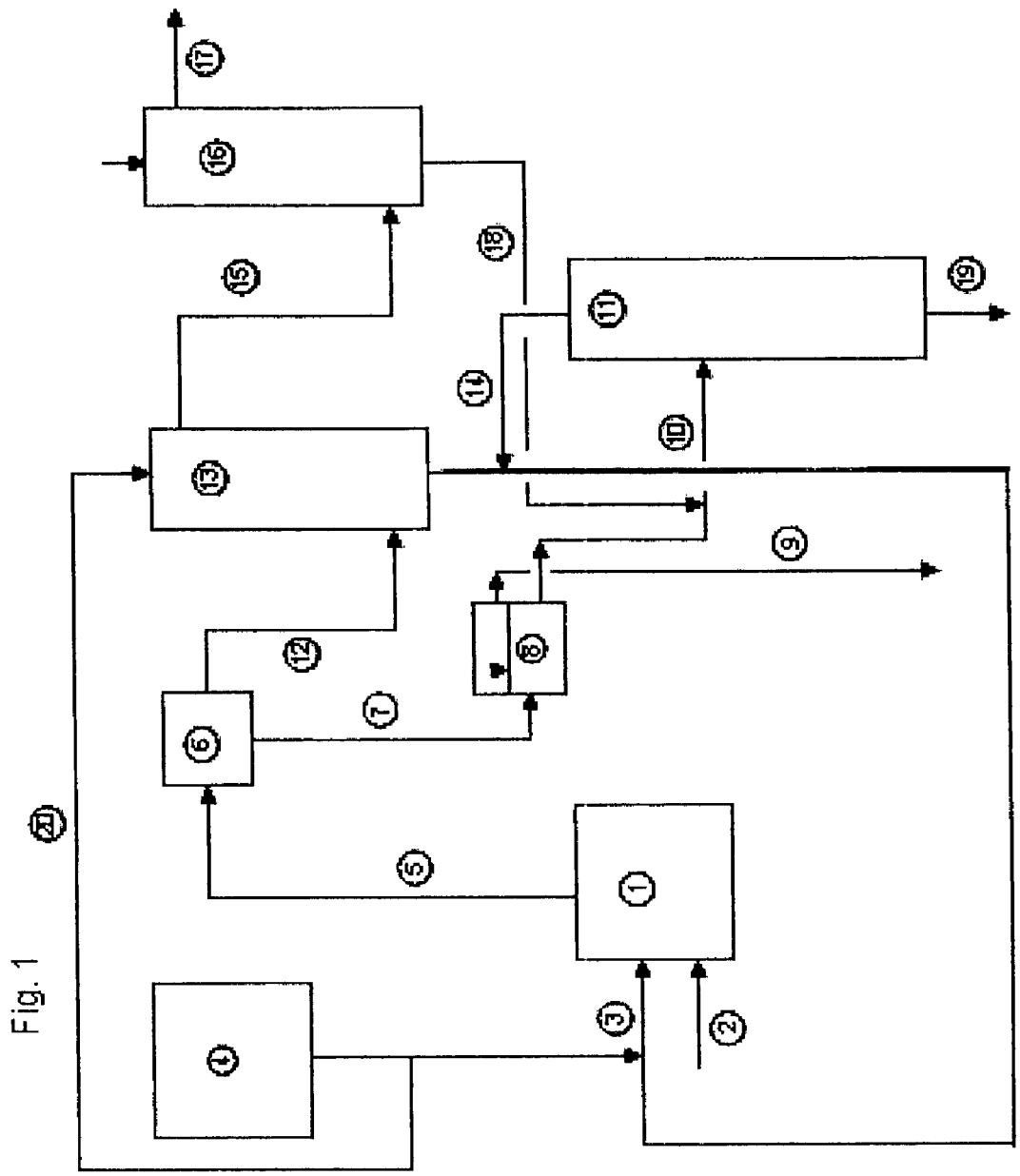
FIG. 1 illustrates in schematic form one embodiment of the subject invention process.

The process makes it possible substantially to separate the Si compounds from the chloromethane formed. The Si compounds separated can be further utilized and no longer interfere with the further process sequence. Environmental pollution is avoided.

Preferably, the reaction of hydrogen chloride with methanol to give chloromethane is carried out in a phase which is liquid under reaction conditions. Preferably, the liquid phase contains catalysts. Preferred catalysts are amine hydrochlorides and the quaternary methylammonium chlorides formed therefrom under process conditions, quaternary phosphonium compounds, and metal chlorides having Lewis acid properties, such as zinc chloride, iron chloride and bismuth oxychloride.

In the process according to the invention, hydrochlorides of primary, secondary, tertiary, linear, cyclic, aliphatic and aromatic amines are preferably used, with the proviso that the catalysts used according to the invention have sufficient thermal stability.

Examples of amines in the amine hydrochloride used according to the invention are ammonia, methylamine, trimethylamine, diethylamine, triethylamine, n-butylamine, tributylamine, ethylenediamine, 1,4-diazabicyclo(2.2.2)octane, 3-dimethylaminopropylamine, diethylenetriamine, aniline and anilines substituted by halogen atoms and/or alkyl groups, such as N,N-dimethylaniline and o-, m-, and p-phenylenediamines, heterocycles such as quinolines, imidazoles, piperidines and piperazines, and pyridine and substituted pyridines, such as pyridines substituted by halogen atoms, alkyl groups and/or amino groups, and the quaternary methylation products thereof with MeCl.

Preferred amines in the amine hydrohalide used according to the invention are the aromatic amines such as anilines, pyridines, quinolines, phenylenediamines and α- and β-naphthylamine, aromatic amines and the methylation products thereof with MeCl which have a low molecular weight being particularly preferred.

Examples of the hydrohalides most preferably used in the process according to the invention are the hydrochlorides of pyridine, 2-methylpyridine, 4-methylpyridine and aniline. The amine hydrochloride used in the process according to the invention can be introduced as such, for example as a mixture with water, into the reactor or can be prepared there from the corresponding amine by reaction with hydrogen halide, the methylation products with MeCl also forming.

The amine hydrochloride used in the process according to the invention may be a single type or a mixture of at least two types of such amine hydrochlorides.

The proportion of catalyst in the liquid phase, based on the total weight of the liquid phase, is preferably from 10 to 80 percent by weight, more preferably from 35 to 60 percent by weight, calculated as the weight of the free amine. Hydrogen chloride is preferably fed in an amount such that the concentration of hydrogen chloride in the liquid phase is below the respective azeotropic concentration.

The liquid-phase reaction is preferably carried out at a temperature of from 90 to 200° C., more preferably from 100 to 180° C., and at a pressure of from 900 to 16,000 hPa, more preferably from 1000 to 6000 hPa, the reaction conditions preferably being chosen so that the volume of the liquid phase remains constant.

In the process according to the invention, methanol is used in excess, preferably 10-50% by weight compared with MeCl, in particular 25-35%.

In the process according to the invention, hydrogen chloride is preferably used in amounts such that the concentration of free hydrogen chloride in the liquid phase is below the respective azeotropic concentration. More preferably, the concentration of free hydrogen chloride in the liquid phase is from 0.1 to 19 percent by weight, in particular from 0.1 to 10 percent by weight, based in each case on the total weight of the liquid phase. The hydrogen chloride not bound to amine is referred to as free hydrogen chloride.

Separation of the condensate into a phase of Si compounds with organic compounds and a methanol/HCl/water phase preferably takes place after the partial removal by condensation of the Si compounds from the chloromethane. The separation of the phases preferably takes place in a separation container. Whether the Si compounds occur as the lighter or heavier phase can be controlled via the composition of the methanol/water phase. The Si compounds separated are preferably metered back into the hydrolysis of the methylchlorosilanes, in particular dimethyldichlorosilane.

The solubility of Si compounds in methanol is influenced by the water content. The preferred water content in the methanol used for washing out the Si compounds is therefore not more than 10% by weight, more preferably not more than 5% by weight, and in particular not more than 2% by weight.

The total methanol used in the process can be used for washing out the Si compounds, or only a portion thereof. Preferably, from 30 to 100%, in particular from 40 to 80%, of the methanol is used for washing out the Si compounds.

The temperature of the methanol for washing out the Si compounds is preferably from 0° C. to 1° C. below its boiling point at the prevailing pressure. The pressure during washing out of the Si compounds with methanol is preferably from 500 to 5000 hPa.

For example, scrubbers with random packings and/or distributor trays can be used for washing out the Si compounds with methanol. Methanol is preferably fed into the upper third of the scrubber. Chloromethane is preferably fed into the lower third of the scrubber.

For improving the separation of entrained methanol, the chloromethane can be passed through suitable condensers and separators for separating off liquid droplets from gases, and the methanol thus separated can be fed back into the methanol scrubber.

The chloromethane escaping from the methanol scrubber is preferably freed from residual methanol in a water scrubber. The methanol from the methanol-containing discharge of the water scrubber is preferably recovered via a distillation column.

A preferred embodiment of the process according to the invention is explained with reference to FIG. 1:

Hydrogen chloride containing Si compounds is fed via line (2) and methanol from the reservoir (4) and the methanol scrubber (13) via line (3) into the heatable reactor (1) which contains catalyst as a mixture with water. The chloromethane formed in the reaction escapes as a mixture with water, methanol, Si compounds and traces of hydrogen chloride into the gas space and passes via line (5) into the condenser (6), where the main amount of water, methanol and Si compounds are separated off as liquid and are fed via line (7) to the separation container (8). In the separation container (8), the Si compounds are separated off as a phase and fed via line (9) for further utilization. The phase comprising predominantly water and methanol is fed via line (10) to the distillation column for methanol recovery (11). The chloromethane removed from the condenser (6) passes via line (12) into the methanol scrubber (13), where it is freed from Si compounds by a countercurrent procedure with fresh methanol from line (20). The methanol which flows out of the methanol scrubber (13) and contains Si compounds is fed, together with the methanol recovered in the distillation column (11) and recycled via line (14), into the reactor (1) via line (3). The chloromethane escaping from the methanol scrubber (13) passes via line (15) into the water scrubber (16), an apparatus in which the chloromethane is freed from methanol by contact with water introduced at the top, and leaves the plant via line (17). The methanol-containing water from the water scrubber (16) is fed via line (18) to the distillation column (11). The water present in the bottom of the distillation column (11) leaves the plant via line (19).

In the following examples and comparative examples, unless stated otherwise in each case, all quantity and percentage data are based on weight and all reactions are carried out at a pressure of 0.10 MPa (abs.).

EXAMPLES

Example 1

Not According to the Invention

Figure 2:
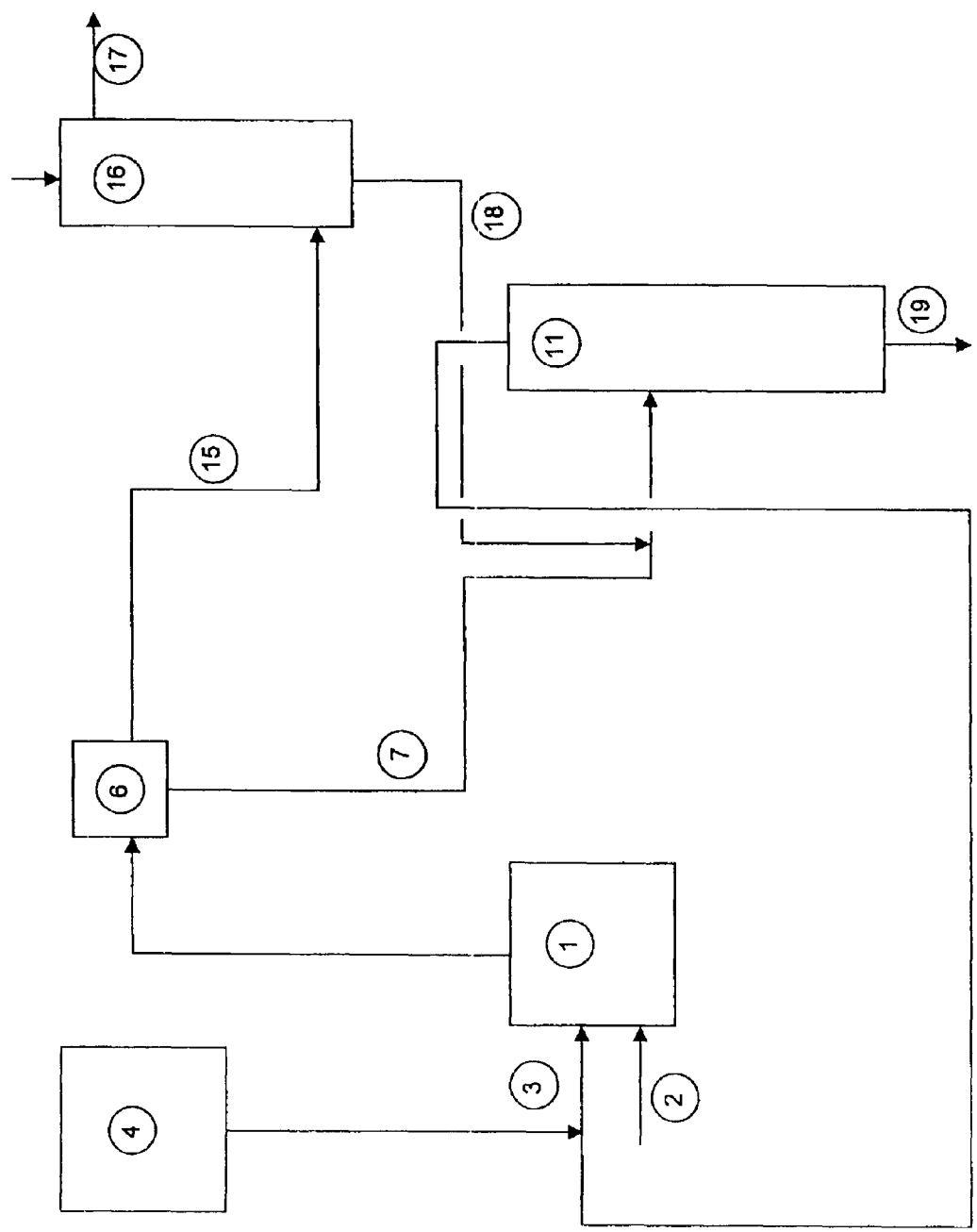
FIG. 2 illustrates a prior art process for preparation of chloromethane.

Chloromethane was prepared in an apparatus analogous to EP 428166 A1, Example 1. The apparatus is illustrated in FIG. 2.

283 l/h of hydrogen chloride containing Si compounds were fed via line (2) and 520 g/h of methanol from the methanol reservoir (4) and the distillation column (11) via line (3) into the heatable reactor (1) which contains catalyst dissolved in hydrochloric acid.

The HCl gas used in the process originated from a plant for the continuous hydrolysis of dimethyldichlorosilane with hydrochloric acid. The purity of the dimethyldichlorosilane was >99.0% by weight.

The content of Si compounds present as impurity in the HCl gas, calculated as $Me_2SiO$, was in total about 2000 ppm. Of this, about 25% were accounted for by the cyclics: 25% of D3, 50% of D4 and about 25% of D6. In addition, traces (<50 ppm) of dimethyldichlorosilane, alpha,omega-dichlorosiloxanes $Cl(Me_2SiO)_nCl$ where n=1-5, and traces of compounds of the type $HO(Me_2Si)_mX$; m=1, 2, 3 . . . ; X=Cl, OH were present.

The following were present as impurities not containing Si: branched C7-hydrocarbons (trimethylbutanes, dimethylpentanes, C7-olefins) and adducts of HCl with these olefins and traces of water.

The concentration of the impurities in the HCl gas was determined by gas chromatography.

The mixture leaving reactor (1) via the top and comprising MeCl, MeOH, traces of dimethyl ether, HCl, Si compounds and hydrocarbons was passed via line (5) into a condenser (6) cooled with ice water, and was cooled to about 10° C., and the condensate formed was collected.

The condensate (about 30% of methanol, 6% of HCl; 63% of water) contained 780 ppm of $Me_2SiO$. Method of measurement: 1H-NMR (ref.: R. Lehnert; NACHR. CHEM. TECH. LAB. 2009(09), 1167-1168).

The condensate was slightly cloudy owing to the Si compounds present. However, phase separation did not occur even after storage for 16 hours. The condensate separated off in the condenser (6) was fed via line (7) to the distillation column (11).

The chloromethane removed from the condenser (6) passed via line (15) into the water scrubber (16). There, the constituents which could not be condensed on passing through the condenser (6) (MeCl, MeOH, DME, water, HCl, Si compounds ($Me_2SiO$)) were washed by a countercurrent procedure with 2000 g/h of water in a column (internal diameter 50 mm, height 1 m) filled with random packings (Berl saddles of ceramic 6×6 mm). An Si determination in the MeCl after water scrubber (16) in line (17) gave an $Me_2SiO$ concentration of 283 ppm.

The discharge (18) of the water scrubber (16) from an experiment of 5 h duration (10.24 kg) was first collected. The discharge contained siloxanes in the form of emulsified finely divided droplets which could not be separated by phase separation even after a relatively long standing time. The $Me_2SiO$ concentration was 240 ppm. The discharge contained about 2.5% of methanol. The collected discharge of the water scrubber (16) and the condensate of the condenser (6) after an experimental duration of 5 h were mixed (about 12 kg) and were metered continuously into the lower part of a heated distillation column (11), a packed column (1 m, 5 cm, Berl saddles of ceramic 6×6 mm), for recovery of methanol. The bottom consisted of a heated 250 ml flask having an overflow through which the level was kept constant. After metering of about 5000 g of methanolic hydrochloric acid having an $Me_2SiO$ content of 310 ppm, blockage by polymeric siloxanes was observed in the vicinity of the metering point in the column. The experiment had to be stopped. The $Me_2SiO$ concentration in the distillate obtained (about 70 g; 10% of water, 90% of MeOH) was about 880 ppm. The distillate of the distillation column (11) was fed via line (3) into the reactor (1).

The bottom discharge from line (19) was cloudy owing to Si compounds present. An $Me_2SiO$ concentration of 155 ppm was measured.

The chloromethane left the plant via line (17).

TABLE 1

Balancing of $Me_2SiO$ in the product streams of an MeCl synthesis from MeOH and HCl (g) with a content of 2000 ppm of $Me_2SiO$ after an experimental duration of 5 h

| Reference numeral | Position | measured $Me_2SiO$ in ppm | calculated $Me_2SiO$ in mg/h |
|---|---|---|---|
| (2) | HCl to MeCl reactor (1) | 2000 | 910 |
| (7) | condensate | 780 | 238 |
| (18) | discharge of water scrubber (16) | 243 | 498 |
| | feed of distillation column (11) | 310 | 736 |
| | top of distillation column (11) | 880 | 116 |
| (19) | bottom of distillation column (11) | 155 | 343 |
| (17) | purified MeCl | 283 | 171 |

87% of the Si compounds introduced via the HCl gas are lost via the wastewater or as an undesired impurity in the MeCl. The content of Si compounds in the methanolic hydrochloric acid obtained as a by product presented difficulties in the working up by distillation with the aim of recovering unreacted methanol.

In the $Me_2SiO$ balance of the methanol recovery, a deficiency of about 1 g=45% of the amount of $Me_2SiO$ introduced was found over an experimental duration of 5 h.

Example 2

According to the Invention

The process was carried out in a plant according to FIG. 1. The HCl gas used for this purpose originated from a plant for the continuous hydrolysis of dimethyldichlorosilane with hydrochloric acid. The purity of the dimethyldichlorosilane was >99.0% by weight.

506 l/h of HCl were reacted with 1070 g/h of MeOH to give 485 l/h of MeCl.

The $Me_2SiO$ concentration in the discharge of the methanol scrubber (13) was about 3500 ppm; (4.28 g/h). The liquid flowing out after cooling of the crude MeCl in the condenser (6) was collected in the separation container (8). A siloxane phase was deposited on the surface (density of the Si phase: 0.91-0.98 g/cm$^3$; 25° C.). The amount of the siloxane phase separated off via line (9) was about 27 g after 24 h. The $Me_2SiO$ concentration in the aqueous methanolic phase of line (10) was 1340 ppm; (0.9 g/h). The phase was slightly cloudy. The quality of the phase separation can be influenced via the density of the aqueous methanolic hydrochloric acid.

The water scrubber (16) was operated as in Example 1 with 2000 g/h of water feed. No $Me_2SiO$ was detectable in the MeCl (of) from line (17) after water scrubber (16). Likewise, no $Me_2SiO$ (<50 ppm) was detectable in the discharge (18) of the water scrubber (16). The outflowing water/methanol mixture was clear.

The discharge (18) of the water scrubber (16), collected within an experimental duration of 24 h, and the methanolic hydrochloric acid from the separation container (8) were mixed and were distilled via the same distillation column (11) as in Example 1. The $Me_2SiO$ concentration in the mixture (10) fed in was 320 ppm.

225 ppm of $Me_2SiO$ (=0.55 g/h) were found in the bottom discharge of the distillation column (11). 1000 ppm; (0.35 g/h) of $Me_2SiO$ were found in the methanol distillate (14). No polymeric siloxane was deposited in the distillation column (11).

TABLE 2

Balancing of $Me_2SiO$ in the product streams of an MeCl synthesis from MeOH and HCl (g) with a content of 2000 ppm of $Me_2SiO$ with $Me_2SiO$ separation after an experimental duration of 24 h

| Reference numeral | Position | $Me_2SiO$ in ppm | $Me_2SiO$ in mg/h |
|---|---|---|---|
| (2) | HCl to MeCl reactor (1) | 2000 | 1600 |
| (7) | condensate | 1340 | 900 |
| (18) | discharge of water scrubber (16) | <50 | ~0 |
| (10) | feed of distillation column (11) | 320 | 900 |
| (14) | top of distillation column (11) | 1000 | 350 |
| (19) | bottom of distillation column (11) | 225 | 550 |
| (17) | purified MeCl | <50 | ~0 |
| | discharge of methanol scrubber (13) | 3500 | 4300 |
| (9) | Si condensate from line (9) | pure | 1100 |

Of the 1.6 g/h of $Me_2SiO$ introduced with the HCl gas, it was possible to separate off 1.1 g/h (68%) by phase separation from the MeOH/HCl/water mixture in separation container F. About 0.50 g/h of $Me_2SiO$ is lost as wastewater via the bottom discharge of the methanol distillation.

The organic phase from the separation container consisted of about 90-99% of Si compounds (mainly cycles D3 to D10). In addition, various, especially branched, C4-C12 alkanes, alkenes, carbonyl compounds, chlorohydrocarbons, EtCl and MeCl were present. The separated Si mixture can be utilized in various ways: for example, it can be fed without further treatment to a reactor for the hydrolysis of dimethyldichlorosilane.

Purely organic impurities present (such as, for example, alkanes, alkenes, carbonyl compounds, chlorohydrocarbons) can be separated from the Si mixture by suitable methods (distillation, extraction, etc.) and the Si compounds remaining behind can be utilized thereafter by feeding into the reactor for the hydrolysis of dimethyldichlorosilane. It is thus possible to separate undesired organic materials from the system of an integrated plant for the preparation of siloxane.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of chloromethane from methanol and hydrogen chloride contaminated with Si compounds, the Si compounds including one or more of methylchlorosilanes, methoxymethylsilanes and hydrolysis and condensation products thereof, comprising removing some of the Si compounds by condensation from the chloromethane formed, washing out remaining Si compounds with methanol and from the methanol thus obtained and containing Si compounds, preparing chloromethane by reaction with hydrogen chloride.

2. The process of claim 1, in which a separation of the condensate from condensation of chloromethane into a phase of Si compounds and organic compounds and a methanol/HCl/water phase takes place after the partial removal by condensation of some of the Si compounds from the chloromethane in a separation container.

3. The process of claim 1, wherein the Si compounds separated are metered into a hydrolysis of the methylchlorosilanes.

4. The process of claim 2, wherein the Si compounds separated are metered into a hydrolysis of the methylchlorosilanes.

5. The process of claim 1, wherein from 30 to 100% of the methanol used in the overall process is used for washing out the Si compounds.

6. The process of claim 2, wherein from 30 to 100% of the methanol used in the overall process is used for washing out the Si compounds.

7. The process of claim 3, wherein from 30 to 100% of the methanol used in the overall process is used for washing out the Si compounds.

8. The process of claim 1, wherein the reaction of hydrogen chloride with methanol to give chloromethane is carried out in a catalyst-containing phase which is liquid under reaction conditions.

9. The process of claim 8, in which amine hydrochlorides are used as catalysts.

\* \* \* \* \*